US007318932B2

(12) United States Patent
Pacetti

(10) Patent No.: US 7,318,932 B2
(45) Date of Patent: Jan. 15, 2008

(54) COATINGS FOR DRUG DELIVERY DEVICES COMPRISING HYDROLITICALLY STABLE ADDUCTS OF POLY(ETHYLENE-CO-VINYL ALCOHOL) AND METHODS FOR FABRICATING THE SAME

(75) Inventor: Stephen D. Pacetti, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 721 days.

(21) Appl. No.: 10/676,413

(22) Filed: Sep. 30, 2003

(65) Prior Publication Data
US 2005/0070936 A1 Mar. 31, 2005

(51) Int. Cl.
A61F 2/02 (2006.01)
(52) U.S. Cl. ..................... 424/425; 424/423
(58) Field of Classification Search ............... None
See application file for complete search history.

(56) References Cited

U.S. PATENT DOCUMENTS

| 4,329,383 A | 5/1982 | Joh ..................... 428/36 |
| 4,733,665 A | 3/1988 | Palmaz ................ 128/343 |
| 4,800,882 A | 1/1989 | Gianturco ............. 128/343 |
| 4,882,168 A | 11/1989 | Casey et al. .......... 424/468 |
| 4,886,062 A | 12/1989 | Wiktor ................ 128/343 |
| 4,941,870 A | 7/1990 | Okada et al. .......... 600/36 |
| 4,977,901 A | 12/1990 | Ofstead ............... 128/772 |
| 5,112,457 A | 5/1992 | Marchant ............. 204/165 |
| 5,165,919 A | 11/1992 | Sasaki et al. ......... 424/488 |
| 5,272,012 A | 12/1993 | Opolski .............. 428/423.1 |
| 5,292,516 A | 3/1994 | Viegas et al. ......... 424/423 |
| 5,298,260 A | 3/1994 | Viegas et al. ......... 424/486 |
| 5,300,295 A | 4/1994 | Viegas et al. ......... 424/427 |
| 5,306,501 A | 4/1994 | Viegas et al. ......... 424/423 |
| 5,328,471 A | 7/1994 | Slepian ............... 604/101 |
| 5,330,768 A | 7/1994 | Park et al. ............ 424/501 |
| 5,380,299 A | 1/1995 | Fearnot et al. ........ 604/265 |
| 5,417,981 A | 5/1995 | Endo et al. ........... 424/486 |
| 5,447,724 A | 9/1995 | Helmus et al. ........ 424/426 |
| 5,455,040 A | 10/1995 | Marchant ............. 424/426 |
| 5,462,990 A | 10/1995 | Hubbell et al. ....... 525/54.1 |
| 5,464,650 A | 11/1995 | Berg et al. ............ 427/2.3 |
| 5,569,463 A | 10/1996 | Helmus et al. ........ 424/426 |
| 5,578,073 A | 11/1996 | Haimovich et al. ...... 623/1 |
| 5,605,696 A | 2/1997 | Eury et al. ........... 424/423 |
| 5,609,629 A | 3/1997 | Fearnot et al. ......... 623/1 |
| 5,624,411 A | 4/1997 | Tuch .................. 604/265 |
| 5,628,730 A | 5/1997 | Shapland et al. ....... 604/21 |
| 5,649,977 A | 7/1997 | Campbell .............. 623/1 |
| 5,658,995 A | 8/1997 | Kohn et al. ........... 525/432 |
| 5,667,767 A | 9/1997 | Greff et al. .......... 424/9.411 |
| 5,670,558 A | 9/1997 | Onishi et al. ......... 523/112 |
| 5,679,400 A | 10/1997 | Tuch ................. 427/2.14 |
| 5,700,286 A | 12/1997 | Tartaglia et al. ........ 623/1 |
| 5,702,754 A | 12/1997 | Zhong ............... 427/2.12 |
| 5,716,981 A | 2/1998 | Hunter et al. ......... 514/449 |
| 5,735,897 A | 4/1998 | Buirge ................ 623/12 |
| 5,746,998 A | 5/1998 | Torchilin et al. ....... 424/9.4 |
| 5,776,184 A | 7/1998 | Tuch ................... 623/1 |
| 5,788,979 A | 8/1998 | Alt et al. ............. 424/426 |
| 5,800,392 A | 9/1998 | Racchini .............. 604/96 |
| 5,820,917 A | 10/1998 | Tuch .................. 427/2.1 |
| 5,824,048 A | 10/1998 | Tuch ................... 623/1 |
| 5,824,049 A | 10/1998 | Ragheb et al. ......... 623/1 |
| 5,830,178 A | 11/1998 | Jones et al. ........... 604/49 |
| 5,837,008 A | 11/1998 | Berg et al. ............ 623/1 |
| 5,837,313 A | 11/1998 | Ding et al. .......... 427/2.21 |
| 5,851,508 A | 12/1998 | Greff et al. ......... 424/9.411 |
| 5,858,746 A | 1/1999 | Hubbell et al. ........ 435/177 |
| 5,865,814 A | 2/1999 | Tuch .................. 604/265 |
| 5,869,127 A | 2/1999 | Zhong ............... 427/2.12 |
| 5,873,904 A | 2/1999 | Ragheb et al. ......... 623/1 |
| 5,876,433 A | 3/1999 | Lunn .................. 623/1 |
| 5,877,224 A | 3/1999 | Brocchini et al. ...... 514/772.2 |
| 5,925,720 A | 7/1999 | Kataoka et al. ........ 525/523 |
| 5,955,509 A | 9/1999 | Webber et al. ......... 514/772.7 |
| 5,971,954 A | 10/1999 | Conway et al. ......... 604/96 |
| 5,980,928 A | 11/1999 | Terry ................. 424/427 |

(Continued)

FOREIGN PATENT DOCUMENTS

EP  0 301 856  2/1989

(Continued)

OTHER PUBLICATIONS

Anonymous, *Cardiologists Draw—Up The Dream Stent*, Clinica 710:15 (Jun. 17, 1996), http://www.dialogweb.com/cgi/document?req=1061848202959, printed Aug. 25, 2003 (2 pages).

(Continued)

*Primary Examiner*—Carlos A. Azpuru
(74) *Attorney, Agent, or Firm*—Squire, Sanders & Dempsey L.L.P.

(57) ABSTRACT

A polymer coating for medical devices based on a derivatized poly(ethylene-co-vinyl alcohol) is disclosed. A variety of polymers are described to make coatings for medical devices, particularly, for drug delivery stents. The polymers include poly(ethylene-co-vinyl alcohol) modified by alkylation, esterification, and introduction of fluorinated alkyl fragments, polysiloxane fragments and poly(ethylene glycol) fragments into the macromolecular chains of poly(ethylene-co-vinyl alcohol).

5 Claims, No Drawings

U.S. PATENT DOCUMENTS

| | | | |
|---|---|---|---|
| 5,980,972 A | 11/1999 | Ding | 427/2.24 |
| 5,997,517 A | 12/1999 | Whitbourne | 604/265 |
| 6,010,530 A | 1/2000 | Goicoechea | 623/1 |
| 6,015,541 A | 1/2000 | Greff et al. | 424/1.25 |
| 6,033,582 A | 3/2000 | Lee et al. | 216/37 |
| 6,042,875 A | 3/2000 | Ding et al. | 427/2.24 |
| 6,051,576 A | 4/2000 | Ashton et al. | 514/255 |
| 6,051,648 A | 4/2000 | Rhee et al. | 525/54.1 |
| 6,056,993 A | 5/2000 | Leidner et al. | 427/2.25 |
| 6,060,451 A | 5/2000 | DiMaio et al. | 514/13 |
| 6,060,518 A | 5/2000 | Kabanov et al. | 514/781 |
| 6,080,488 A | 6/2000 | Hostettler et al. | 428/423.3 |
| 6,096,070 A | 8/2000 | Ragheb et al. | 623/1 |
| 6,099,562 A | 8/2000 | Ding et al. | 623/1.46 |
| 6,110,188 A | 8/2000 | Narciso, Jr. | 606/153 |
| 6,110,483 A | 8/2000 | Whitbourne et al. | 424/423 |
| 6,113,629 A | 9/2000 | Ken | 623/1.1 |
| 6,120,536 A | 9/2000 | Ding et al. | 623/1.43 |
| 6,120,904 A | 9/2000 | Hostettler et al. | 428/423.3 |
| 6,121,027 A | 9/2000 | Clapper et al. | 435/180 |
| 6,129,761 A | 10/2000 | Hubbell | 623/11 |
| 6,153,252 A | 11/2000 | Hossainy et al. | 427/2.3 |
| 6,165,212 A | 12/2000 | Dereume et al. | 623/1.13 |
| 6,203,551 B1 | 3/2001 | Wu | 606/108 |
| 6,231,600 B1 | 5/2001 | Zhong | 623/1.42 |
| 6,240,616 B1 | 6/2001 | Yan | 29/527.2 |
| 6,245,753 B1 | 6/2001 | Byun et al. | 514/56 |
| 6,251,136 B1 | 6/2001 | Guruwaiya et al. | 623/1.46 |
| 6,254,632 B1 | 7/2001 | Wu et al. | 623/1.15 |
| 6,258,121 B1 | 7/2001 | Yang et al. | 623/1.46 |
| 6,283,947 B1 | 9/2001 | Mirzaee | 604/264 |
| 6,283,949 B1 | 9/2001 | Roorda | 604/288.02 |
| 6,284,305 B1 | 9/2001 | Ding et al. | 427/2.28 |
| 6,287,628 B1 | 9/2001 | Hossainy et al. | 427/2.3 |
| 6,299,604 B1 | 10/2001 | Ragheb et al. | 604/265 |
| 6,306,176 B1 | 10/2001 | Whitbourne | 623/23.59 |
| 6,331,313 B1 | 12/2001 | Wong et al. | 424/427 |
| 6,335,029 B1 | 1/2002 | Kamath et al. | 424/423 |
| 6,346,110 B2 | 2/2002 | Wu | 606/108 |
| 6,358,556 B1 | 3/2002 | Ding et al. | 427/2.24 |
| 6,379,381 B1 | 4/2002 | Hossainy et al. | 623/1.42 |
| 6,395,326 B1 | 5/2002 | Castro et al. | 427/2.24 |
| 6,419,692 B1 | 7/2002 | Yang et al. | 623/1.15 |
| 6,451,373 B1 | 9/2002 | Hossainy et al. | 427/2.25 |
| 6,494,862 B1 | 12/2002 | Ray et al. | 604/96.01 |
| 6,503,556 B2 | 1/2003 | Harish et al. | 427/2.24 |
| 6,503,954 B1 | 1/2003 | Bhat et al. | 514/772.2 |
| 6,506,437 B1 | 1/2003 | Harish et al. | 427/2.25 |
| 6,527,801 B1 | 3/2003 | Dutta | 623/1.46 |
| 6,527,863 B1 | 3/2003 | Pacetti et al. | 118/500 |
| 6,540,776 B2 | 4/2003 | Sanders Millare et al. | 623/1.15 |
| 6,544,223 B1 | 4/2003 | Kokish | 604/103.01 |
| 6,544,543 B1 | 4/2003 | Mandrusov et al. | 424/422 |
| 6,544,582 B1 | 4/2003 | Yoe | 427/2.24 |
| 6,555,157 B1 | 4/2003 | Hossainy | 427/2.24 |
| 6,558,733 B1 | 5/2003 | Hossainy et al. | 427/2.24 |
| 6,565,659 B1 | 5/2003 | Pacetti et al. | 118/500 |
| 6,572,644 B1 | 6/2003 | Moein | 623/1.11 |
| 6,585,765 B1 | 7/2003 | Hossainy et al. | 623/1.45 |
| 6,585,926 B1 | 7/2003 | Mirzaee | 264/400 |
| 2001/0018469 A1 | 8/2001 | Chen et al. | 523/121 |
| 2001/0037145 A1 | 11/2001 | Guruwaiya et al. | 623/1.15 |
| 2002/0077693 A1 | 6/2002 | Barclay et al. | 623/1.13 |
| 2002/0091433 A1 | 7/2002 | Ding et al. | 623/1.2 |
| 2002/0155212 A1 | 10/2002 | Hossainy | 427/2.25 |
| 2003/0065377 A1 | 4/2003 | Davila et al. | 623/1.13 |
| 2003/0099712 A1 | 5/2003 | Jayaraman | 424/486 |

FOREIGN PATENT DOCUMENTS

| | | |
|---|---|---|
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 273 314 | 1/2003 |
| JP | 2001-190687 | 7/2001 |
| WO | WO 91/12846 | 9/1991 |
| WO | WO 95/10989 | 4/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/17331 | 4/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 02/078668 | 10/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 2004/022119 | 3/2004 |

OTHER PUBLICATIONS

Anonymous, *Heparin-coated stents cut complications by 30%*, Clinica 732:17 (Nov. 18, 1996), http://www.dialogweb.com/cgi/document?req=1061847871753, printed Aug. 25, 2003 (2 pages).

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting continues to dominate cardiology*, Clinica 720:22 (Sep. 2, 1996), http://www.dialogweb.com/cgi/document?req=1061848017752, printed Aug. 25, 2003 (2 pages).

Aoyagi et al., *Preparation of cross-linked aliphatic polyester and application to thermo-responsive material*, Journal of Controlled Release 32:87-96 (1994).

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of commercially available materials with a new heparinizable material*, J. Biomed. Mater. Res. 25:1259-1274 (Oct. 1991).

Chung et al., *Inner core segment design for drug delivery control of thermo-responsive polymeric micelles*, Journal of Controlled Release 65:93-103 (2000).

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).

Dichek et al., *Seeding of Intravascular Stents with Genetically Engineered Endothelial Cells*, Circ. 80(5):1347-1353 (Nov. 1989).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Inoue et al., *An AB block copolymer of oligo(methyl methacrylate) and poly(acrylic acid) for micellar delivery of hydrophobic drugs*, Journal of Controlled Release 51:221-229 (1998).

Kataoka et al., *Block copolymer micelles as vehicles for drug delivery*, Journal of Controlled Release 24:119-132 (1993).

Levy et al., *Strategies For Treating Arterial Restenosis Using Polymeric Controlled Release Implants*, Biotechnol. Bioact. Polym. [Proc. Am. Chem. Soc. Symp.], pp. 259-268 (1994).

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18(12):885-890 (1997).

Matsumaru et al., *Embolic Materials For Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Nordrehaug et al., *A novel biocompatible coating applied to coronary stents*, European Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sep./Oct. 1996).

Pechar et al., *Poly(ethylene glycol) Multiblock Copolymer as a Carrier of Anti-Cancer Drug Doxorubicin*, Bioconjugate Chemistry 11(2):131-139 (Mar./Apr. 2000).

Peng et al., *Role of polymers in improving the results of stenting in coronary arteries*, Biomaterials 17:685-694 (1996).

Shigeno, *Prevention of Cerebrovascular Spasm By Bosentan, Novel Endothelin Receptor*, Chemical Abstract 125:212307 (1996).

van Beusekom et al., *Coronary stent coatings*, Coronary Artery Disease 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

Huang et al., *Synthesis and Characterization of Self-Assembling Block Copolymers Containing Bioadhesive/End Groups*, Biomacromolecules vol. 3, No. 2, 397-406 (2002).

COATINGS FOR DRUG DELIVERY DEVICES COMPRISING HYDROLITICALLY STABLE ADDUCTS OF POLY(ETHYLENE-CO-VINYL ALCOHOL) AND METHODS FOR FABRICATING THE SAME

BACKGROUND

1. Field of the Invention

This invention relates to the field of medical devices, especially drug delivery devices such as drug eluting vascular stents.

2. Description of the State of the Art

A stent is a tubular scaffolding structure used to mechanically uphold the patency of the lumen in which the stent is placed. Stents are being modified to also provide pharmacological therapy. One method of medicating a stent is with the use of a polymer coating impregnated with a drug. A variety of polymers can be used to coat stents. Of particular interest is a copolymer of ethylene and vinyl alcohol, also known as poly(ethylene-co-vinyl alcohol) having a general formula —[CH$_2$—CH$_2$]$_m$—[CH$_2$—CH(OH)]$_n$—. Poly(ethylene-co-vinyl alcohol) is also known under the trade name EVAL and is distributed commercially by Aldrich Chemical Company of Milwaukee, Wis. EVAL is also manufactured by EVAL Company of America of Lisle, Ill.

EVAL possesses a desirable impermeability to oxygen, is biologically compatible, and adheres well to metals, such as stainless steel. At the same time, the biological compatibility of EVAL can be improved. One way to improve the biological compatibility of EVAL can be by forming an adduct of EVAL with a compound that can provide enhanced biological compatibility. Such highly biologically compatible compounds include poly(alkylene glycols) one example of which is poly(ethylene glycol)(PEG). For example, EVAL can be derivatized by having PEG conjugated to EVAL to form an EVAL-PEG adduct. The EVAL-PEG adduct is expected to have improved biological compatibility, for example, to have non-fouling properties. The term "non-fouling property" refers to the ability of the stent surface to prevent or at least reduce a build-up of a thick, denatured layer of protein which typically tends to accumulate on the surface of a bare metal stent or a stent coated with polymers such as EVAL. Such accumulation or "fouling" of the stent surface is a result of the body's reaction to a foreign material. The fouling of the stent surface is undesirable for long-term tissue compatibility.

While PEG-modified EVAL is expected to have improved biological compatibility including non-fouling property, some further improvements are desirable. In particular, PEG can disappear quickly from the EVAL-PEG adduct as a result of hydrolysis, if PEG is attached to EVAL via hydrolytically unstable links such as anhydride, ester, orthoester or acetal bonds. As a result, the duration of service of the EVAL-PEG based coating can be less than optimal.

In view of the foregoing, it is desirable to have hydrolytically stable biologically compatible derivatives of EVAL having non-fouling properties. The present invention provides such derivatives.

SUMMARY

A medical article is provided, the medical article comprises an implantable substrate having a coating deposited on at least a portion of the substrate, the coating comprising a polymer having the formula:

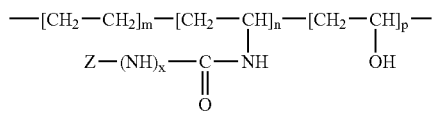

wherein Z is a non-fouling moiety. The non-fouling moiety can be a derivative of a compound selected from a poly (alkylene glycol), heparin, poly(vinyl pyrrolidone), poly(2-hydroxyethylmethacrylate), poly(2-hydroxypropyl methacrylamide), poly(styrene sulfonate), hyaluronic acid, chondroitan sulfate, and chitosan. Examples of the poly (alkylene glycol)s that can be used include poly(ethylene glycol), poly(1-propylene glycol), poly(2-propylene glycol) and poly(tetramethylene glycol).

A method for fabricating a medical article is provided, the method includes synthesizing a polymer having a formula:

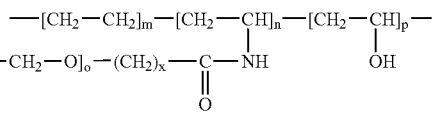

wherein X is hydrogen or methyl and the synthesis comprises preparing a primary amino-functional poly(ethylene vinyl alcohol), and reacting the primary amino-functional poly(ethylene vinyl alcohol) with a succinimidyl derivative of poly(ethylene glycol).

A method for fabricating a medical article is provided, the method includes synthesizing a polymer having a formula:

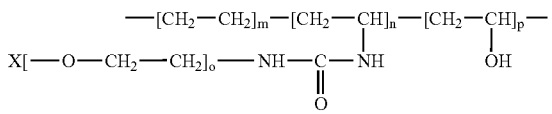

wherein X is hydrogen or methyl and the synthesis comprises preparing a primary amino-functional poly(ethylene vinyl alcohol), and reacting the primary amino-functional poly(ethylene vinyl alcohol) with an isocyanate derivative of poly(ethylene glycol).

A method for fabricating a medical article is provided, the method includes synthesizing a polymer having a formula:

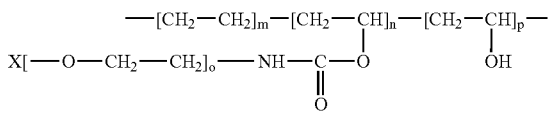

wherein X is hydrogen or methyl and the synthesis comprises reacting poly(ethylene glycol) or methoxylated poly (ethylene glycol) with N,N'-disuccinimidyl carbonate or with an aliphatic diisocyanate to obtain an activated derivative of poly(ethylene glycol) or methoxylated poly(ethylene glycol), and reacting the activated derivative of poly(ethylene glycol) or methoxylated poly(ethylene glycol) with poly(ethylene-co-vinyl alcohol).

A method for fabricating a medical article is provided, the method includes synthesizing a polymer having a formula:

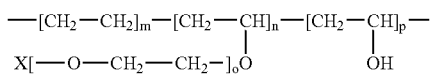

wherein X is hydrogen or methyl and the synthesis comprises reacting poly(ethylene glycol) or methoxylated poly(ethylene glycol) with 1,4-dibromo-n-butane or with bis-epoxide to obtain an activated derivative of methoxylated poly(ethylene glycol), and reacting the activated derivative of poly(ethylene glycol) or methoxylated poly(ethylene glycol) with poly(ethylene-co-vinyl alcohol).

A method for fabricating a medical article is provided, the method includes synthesizing a polymer having a formula:

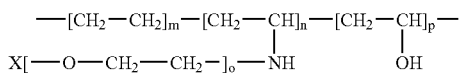

wherein X is hydrogen or methyl and the synthesis comprises oxidizing poly(ethylene-co-vinyl alcohol) to obtain an activated derivative of poly(ethylene-co-vinyl alcohol), and reacting the activated derivative of poly(ethylene-co-vinyl alcohol) with poly(ethylene glycol)-amine adduct.

A method for fabricating a medical article is provided, the method includes synthesizing a polymer having a formula:

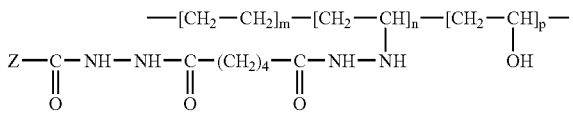

wherein Z is a moiety derived from hyaluronic acid and the synthesis comprises oxidizing poly(ethylene vinyl alcohol) to form a poly(ethylene vinyl alcohol) having ketone groups, preparing a dihydrazide derivative of hyaluronic acid, and reacting the poly(ethylene vinyl alcohol) having ketone groups with the dihydrazide derivative of hyaluronic acid.

A method for fabricating a medical article is provided, the method includes synthesizing a polymer having a formula:

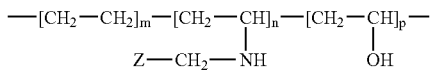

wherein Z is a moiety derived from heparin and the synthesis comprises preparing a primary amino-functional poly(ethylene vinyl alcohol), and reacting the primary amino-functional poly(ethylene vinyl alcohol) with an aldehyde-terminated derivative of heparin.

A method for fabricating a medical article is provided, the method includes synthesizing a polymer having a formula:

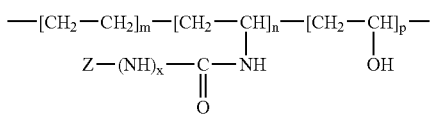

wherein Z is a non-fouling moiety.

DETAILED DESCRIPTION

1. Terms and Definitions

The following definitions apply:

The term "non-fouling moiety" is defined as portion of a chemical compound that is capable of providing the compound with the ability to prevent or at least reduce a build-up of a denatured layer of protein on the stent surface or on the stent coating.

The term "non-fouling complex" refers to polymeric substances such as polymeric conjugates and/or polymeric adducts that comprise a non-fouling moiety.

The term "conjugated" is defined as "linked," for example, covalently linked. The term "conjugating" is defined as a process of forming a link, for example, a covalent link.

The term "pegylation" is defined as the process of bonding poly(ethylene glycol) (PEG) to poly(ethylene-co-vinyl alcohol) (EVAL) to form an EVAL/PEG adduct.

The term "hydrolytically stable" is defined as the ability of a compound (e.g., a polymer or a polymeric adduct) to be exposed to aqueous fluids having pH near neutral (e.g., blood), without being substantially hydrolyzed for a period of time of at least 1 to 6 months. The temperature of an aqueous liquid to which a compound is exposed can be between a room temperature and about 36° C. "Substantially hydrolyzed" is defined as losing about 20% or more of the polymer (by mass) to hydrolysis. One way of determining whether a polymer or a polymeric adduct is hydrolytically stable can include (a) depositing the polymer or adduct on a stent to make the polymer-coated stent; (b) weighing the polymer-coated stent; (c) immersing the polymer-coated stent into an aqueous fluid having pH near neutral; and (d) periodically weighing the stent. If after 1 to 6 months of such exposure about 80% (by mass) or more of the polymer or adduct still remains on the stent, the polymer or adduct is defined as "hydrolytically stable."

The term "polymer-analogous transformation" is defined as a synthetic process of replacing functional groups in a macromolecule of the original polymer with other functional groups thus making a new polymer having new properties. The new polymer, however, retains many features of the original polymer, such as the original degree of polymerization and the structure of the backbone of the original polymer (including linear or branched nature) after the process of polymer-analogous transformation is completed.

2. Embodiments of the Invention

A coating for an implantable medical device, such as a stent, according to embodiments of the present invention, can be a multi-layered structure that can include any or all of the following three layers:

(a) a drug-polymer layer (also referred to as "reservoir" or "reservoir layer"), comprising a copolymer and a drug, or alternatively a copolymer free drug layer;

(b) a primer layer; and/or (c) a topcoat layer.

Each layer of the stent coating can be formed by dissolving the copolymer or a blend of copolymers in a solvent, or a mixture of solvents, and applying the resulting copolymer solution on the stent by spraying or immersing the stent in the solution. After the solution has been applied onto the stent, the coating is dried by allowing the solvent to evaporate. The process of drying can be accelerated if the drying is conducted at an elevated temperature.

To incorporate a drug into the reservoir layer, the drug can be combined with the copolymer solution that is applied onto the stent as described above. Alternatively, to fabricate a copolymer-free drug layer, the drug can be dissolved in a suitable solvent or mixture of solvents, and the resulting drug solution can be applied on the stent by spraying or immersing the stent in the drug solution.

Instead of introducing the drug as a solution, the drug can be introduced as a colloid system, such as a suspension in an appropriate solvent phase. To make the suspension, the drug can be dispersed in the solvent phase using conventional techniques used in colloid chemistry. Depending on a variety of factors, e.g., the nature of the drug, those having ordinary skill in the art can select the solvent to form the solvent phase of the suspension, as well as the quantity of the drug to be dispersed in the solvent phase. The suspension can be mixed with a copolymer solution and the mixture can be applied on the stent as described above. Alternatively, the drug suspension can be applied on the stent without being mixed with the copolymer solution.

The drug-polymer layer can be applied directly onto at least a part of the stent surface to serve as a reservoir for at least one active agent or a drug which is incorporated into the reservoir layer. The primer layer can be applied between the stent and the reservoir to improve the adhesion of the drug-polymer layer to the stent. The topcoat layer can be applied over at least a portion of the reservoir layer and serves as a rate limiting membrane which helps to control the rate of release of the drug. The topcoat layer can be essentially free from any active agents or drugs.

According to embodiments of the present invention, any or all of the layers of the stent coating can be made of derivatives of EVAL, the derivatives having improved biological compatibility and non-fouling properties. To obtain the derivatives, EVAL can be modified by reactions of polymer-analogous transformation.

According to one embodiment of the present invention, EVAL can be derivatized using a polymer-analogous transformation process of hydrophilic modification. According to this process, EVAL can be derivatized by having a non-fouling moiety conjugated to EVAL via hydrolytically stable linkages to form a non-fouling EVAL complex. The non-fouling moieties can include (a) poly(alkylene glycols) or (b) molecules other than poly(alkylene glycols). For example, a poly(alkylene glycol) can be conjugated to EVAL to form a non-fouling EVAL/poly(alkylene glycol) complex.

One example of a poly(alkylene glycol) that can be bonded to EVAL is poly(ethylene glycol)(PEG). As a result of conjugating PEG to EVAL (pegylation), a non-fouling EVAL/PEG complex can be obtained, and the biological compatibility of EVAL can be improved. Examples of other poly(alkylene glycols) that can be conjugated to EVAL include poly(1-propylene glycol), poly(2-propylene glycol) and poly(tetramethylene glycol).

Examples of non-fouling moieties other than poly(alkylene glycols) that can be conjugated to EVAL to form a non-fouling EVAL complex include heparin, poly(vinyl pyrrolidone), poly(2-hydroxyethylmethacrylate), poly(2-hydroxypropylmethacrylamide), poly(styrene sulfonate), hyaluronic acid, chondroitan sulfate, and chitosan.

The EVAL/PEG adducts of the present invention can be hydrolytically stable. To synthesize hydrolytically stable EVAL/PEG adducts, the process of pegylation can be carried to form a macromolecule of EVAL connected to a macromolecule of PEG via hydrolytically stable chemical links. Examples of such links include amide, urethane, urea, ether, aliphatic carbonate, or amine bonds. Polymers of these invention, which are EVAL/PEG adducts having these hydrolytically stable links, are schematically shown in Table 1.

TABLE 1

Examples of Hydrolytically Stable EVAL/PEG Adducts

| Link | Adduct (Schematically) | Adduct (Exemplary Formula) |
|------|------------------------|-----------------------------|
| Amide | EVAL-NH—C(=O)-PEG | —$[CH_2-CH_2]_m$—$[CH_2-CH]_n$—$[CH_2-CH]_p$— <br> $XO[-CH_2-CH_2-O]_o-(CH_2)_x-C(=O)-NH$   OH |
| Urethane | EVAL-O—C(=O)—NH-PEG | —$[CH_2-CH_2]_m$—$[CH_2-CH]_n$—$[CH_2-CH]_p$— <br> $X[-O-CH_2-CH_2]_o-NH-C(=O)-O$   OH |

TABLE 1-continued

Examples of Hydrolytically Stable EVAL/PEG Adducts

| Link | Adduct (Schematically) | Adduct (Exemplary Formula) |
|---|---|---|
| Urea | EVAL-NH—C(=O)—NH-PEG |  |
| Ether | EVAL-O-PEG |  |
| Carbonate | EVAL-O—C(=O)—O-PEG |  |
| Amine | EVAL-NH-PEG |  |

In compounds of Table 1, X is hydrogen or methyl, and each of m, n, o, independently, is a positive integer, and p is either a positive integer or zero. The value of m can be within a range of between about 30 and about 7,600; the value of o can be within a range of between about 11 and about 680; the value of the sum of n and p can be within a range of between about 30 and about 7,600, and the value of the sum of m, n and p can be within a range of between about 700 and about 7,600. If p≠0, a ratio between n and p can be between about 1:19 and about 1:3.

Methods of synthesizing the EVAL/PEG adducts shown in Table 1 are described in the Examples provided below.

For derivatization by the reactions of polymer-analogous transformation, EVAL with concentration of about 56 molar % of vinyl units (corresponding to about 67 mass %) can be used. Other brands of EVAL can be selected according to the criteria chosen by those having ordinary skill in the art. The degree of derivatization of EVAL need not be high. Derivatization of between about 5% and about 25%, for example, about 10% of the vinyl-alcohol-derived units of EVAL can be sufficient.

Polymers of this invention can be used as a coating on a medical device, particularly, on a drug delivery stent. The coating can be applied onto the stent by a commonly used method known to one of ordinary skill in the art, for instance, by spraying, dipping or molding. The drug can be incorporated within the coating, or the drug can be in a separate layer underneath the coating, or the drug can be adsorbed onto the surface of the coating. The coating can also be used as a primer layer or a topcoat layer.

The embodiments of the present invention are described in connection with a stent, e.g., balloon expandable or self-expandable stents; however, other implantable medical devices can also be used. The stent, or other implantable medical device can be used in any part of the vascular system, including neurological, carotid, coronary, renal, aortic, iliac, femoral or any other part of the peripheral vasculature. There are no limitations on the size of the stent, its length, diameter, strut thickness or pattern. Examples of other implantable devices include stent-grafts, grafts (e.g., aortic grafts), artificial heart valves, cerebrospinal fluid shunts, pacemaker electrodes, and endocardial leads (e.g., FINELINE and ENDOTAK, available from Guidant Corp. of Santa Clara, Calif.). The underlying structure of the device can be of virtually any design. The device can be made of a metallic material or an alloy such as, but not limited to, cobalt chromium alloy (ELGILOY), stainless steel (316L), cobalt chromium alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co. of Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

The therapeutic substance or drug can include any substance capable of exerting a therapeutic or prophylactic effect in the practice of the present invention. The drug may include small molecule drugs, peptides or proteins. The drug can be for inhibiting abnormal or inappropriate migration and proliferation of smooth muscular cells for the treatment of restenosis.

Examples of therapeutic substances that can be used include antiproliferative substances such as actinomycin D, or derivatives and analogs thereof (manufactured by Sigma-Aldrich of Milwaukee, Wis., or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S. A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as ANGIOMAX (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, tacrolimus, dexamethasone, and rapamycin and structural derivatives or functional analogs thereof, such as 40-O-(2-hydroxy)ethyl-rapamycin (known by the trade name of EVEROLIMUS available from Novartis), 40-O-(3-hydroxy)propyl-rapamycin, 40-O-[2-(2-hydroxy)ethoxy]ethyl-rapamycin, and 40-O-tetrazole-rapamycin.

EXAMPLES

The following examples demonstrate the processes used to derivatize EVAL to make coatings for medical devices.

Example 1

Synthesis of EVAL/PEG Adduct with Ether Links

EVAL can be modified by reacting with PEG having a general formula $HO-[CH_2-CH_2-O]_o-X$, wherein X is hydrogen or methyl. Due to the presence of the hydroxyl group, PEG is capable of entering reactions of condensation with EVAL to form ether links. One possible path of the condensation reaction can be summarized schematically by the net pegylation reaction (I):

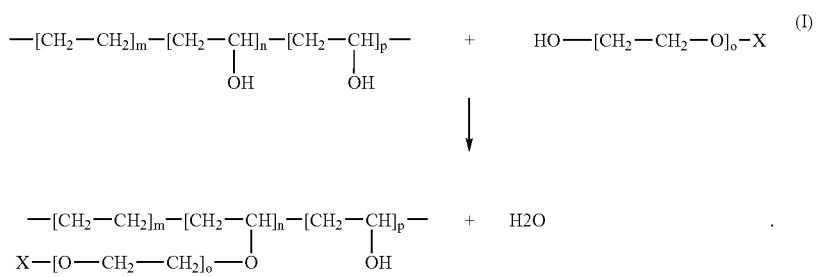

PEG can be in an oligomeric or polymeric form and can have a molecular weight within a range of between about 500 and about 30,000 Daltons, corresponding to the values of o of between about 11 and about 680. Optionally, the product of reaction (I) can include a spacer group between the fragment derived from PEG, shown in reaction (I) as $X-[O-CH_2-CH_2]_o-O-$, and the fragment derived from EVAL. The spacer group can be an alkyl group or hydroxylated alkyl group as described in more detail below.

To carry out the reaction (I), methoxylated PEG (mPEG) in which $X=CH_3$, can be used. mPEG is available from Nektar Corp. (formerly, Shearwater Corp.) of Huntsville, Ala. The synthesis can include two steps, (a) an activation step and (b) a condensation step.

Activation Step

In the activation step, the mPEG is added to a solution of an activating compound, for example, 1,4-dibromo-n-butane $Br-(CH_2)_4-Br$ or bis-epoxide. The activating compound can be present in excess. After the reaction, unreacted activating compound can be removed from the activated mPEG by solvent extraction.

For example, mPEG can be activated by a reaction of alkylation. To carry out the alkylation reaction, a halogenated reagent, such as 1,4-dibromo-n-butane can be used. The path of alkylation is expected to include an attack of 1,4-dibromo-n-butane directed to the terminal hydroxyl of mPEG, yielding a brominated derivative of mPEG, as shown by the reaction scheme (II):

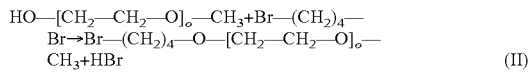

(II)

Alternatively, instead of 1,4-dibromo-n-butane, bis-epoxide can be used in the activation step to obtain an epoxylated derivative of MPEG. Bis-epoxide is expected to react with a terminal hydroxyl of mPEG, yielding an epoxylated derivative of mPEG, as shown by the reaction scheme (III):

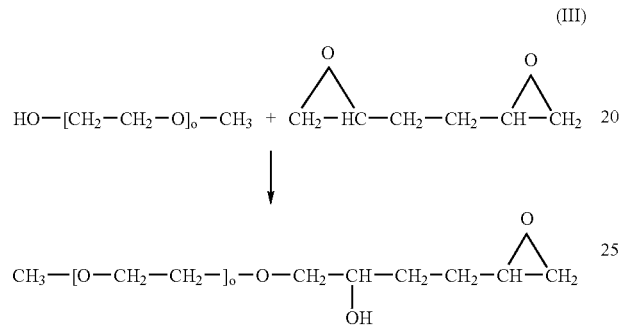

(III)

Condensation Step

As a condensation step, the brominated mPEG or epoxylated mPEG can be reacted with EVAL in the presence of a non-nucleophilic base such as potassium tert-butoxide or 1,4-diazabicyclo[2.2.2]octane to form an EVAL/mPEG adduct. An exemplary reaction for the brominated mPEG is shown by the scheme (IV):

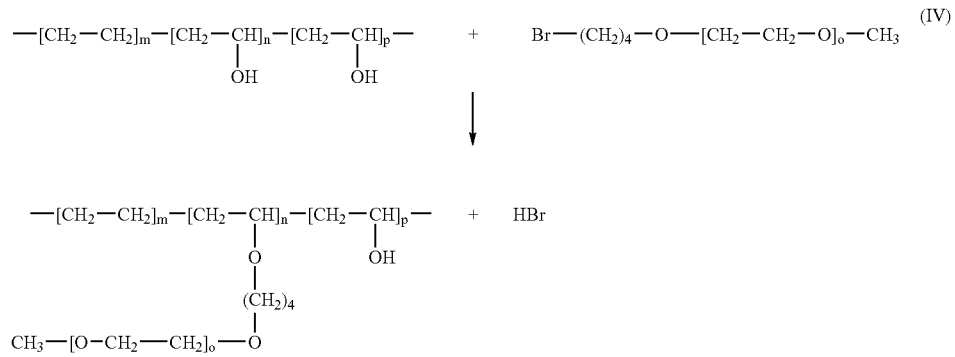

(IV)

As shown by reaction (IV), the final EVAL/mPEG adduct contains a spacer group mentioned above. The spacer group in this case is n-butylene—$(CH_2)_4$—. If an epoxylated derivative of mPEG shown by reaction (III) is used for conjugating mPEG to EVAL, the spacer group is 2,5-dihydroxyhexylene —$CH_2$—$CH(OH)$—$CH_2$—$CH_2$—$CH(OH)$—$CH_2$—. The conditions under which reactions (II), (III) and (IV) are conducted can be determined by those having ordinary skill in the art. As shown by reactions (I) and (IV), the main product of a process of pegylation is an EVAL/mPEG adduct. An EVAL/mPEG adduct is also a product of a process of pegylation where instead of the brominated mPEG, the epoxylated mPEG discussed above is used. In the EVAL/mPEG adduct which is the product of reaction (I), EVAL and mPEG are covalently linked with a hydrolytically stable ether link. The adduct is expected to have long lasting biocompatibility and non-fouling properties.

Example 2

Synthesis of EVAL/PEG Adduct with Amine Links

EVAL can be derivatized by PEG via formation of amine links, and PEG-amine adduct can be used for such modification. Derivatization of EVAL with a PEG-amine adduct is a three-step process. First, EVAL can be activated, for example, by selective oxidation, for example, using chromium trioxide, to form a polymer with a reactive carbonyl moiety, as shown by reaction scheme (V):

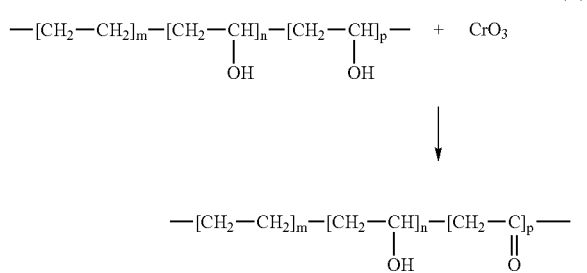

(V)

As a second step of the synthesis, the oxidized EVAL can be reacted with a poly(ethylene glycol)-amine adduct, which is a PEG-based product having amino groups. An example of a PEG-based amino product suitable as a modifier for EVAL is a methoxylated product having a general formula $CH_3$—[O—$CH_2$—$CH_2$]$_o$—$NH_2$ (mPEG-$NH_2$). This product, manufactured by Nektar Corp., can have a molecular weight between about 3,400 and about 5,000, which corresponds to the value of the integer "o" of between about 76 and about 113. The reaction between the oxidized EVAL obtained as described above and mPEG-$NH_2$ is a reaction of amination of the carbonyl moieties obtained as a result of reaction (V).

Following the amination, the third step of reduction is performed, for example, using potassium borohydride $KBH_4$. The second and third step taken together compose the process of reductive amination of oxidized EVAL. The process of reductive amination yields the EVAL/mPEG-$NH_2$ adduct. The summary of the process of reductive amination can be illustrated by the reaction scheme (VI):

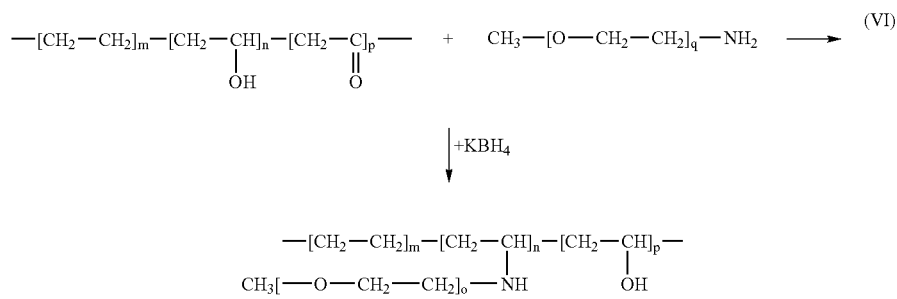

(VI)

Example 3

Synthesis of EVAL/PEG Adduct with Urethane Links

EVAL can be modified by PEG via formation of urethane links. Modification of EVAL with a PEG-amine adduct is a two-step process. First, a PEG-amine adduct can be activated, to obtain a reactive derivative of PEG for example, by reacting with N,N'-disuccinimidyl carbonate shown by formula (VII).

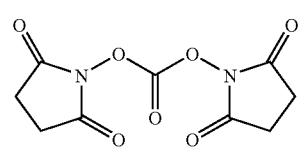

(VII)

The conditions under which reactions (V) and (VI) are conducted can be determined by those having ordinary skill in the art. In the EVAL/mPEG-NH$_2$ adduct which is the product of reaction (VI), EVAL and mPEG are covalently linked in a hydrolytically stable secondary amino structure. The adduct is expected to have long lasting biocompatibility and non-fouling properties.

mPEG-NH$_2$ described above can be used as the PEG-amine adduct. The reaction of activation can be illustrated as shown by the reaction scheme (VIII):

$$CH_3-[O-CH_2-CH_2]_q-NH_2 + SUC-O-C(O)-O-SUC$$
$$\downarrow$$
$$CH_3-[O-CH_2-CH_2]_q-NH-O-C(O)-SUC$$

(VIII)

where "SUC" is an abbreviation standing for the succinimidyl group.

As a second step, the succinimidyl derivative of mPEG-NH$_2$ obtained as a result of reaction (VIII) can be reacted with EVAL. As a result, EVAL is derivatized to form an EVAL/PEG adduct as shown by the reaction scheme (IX):

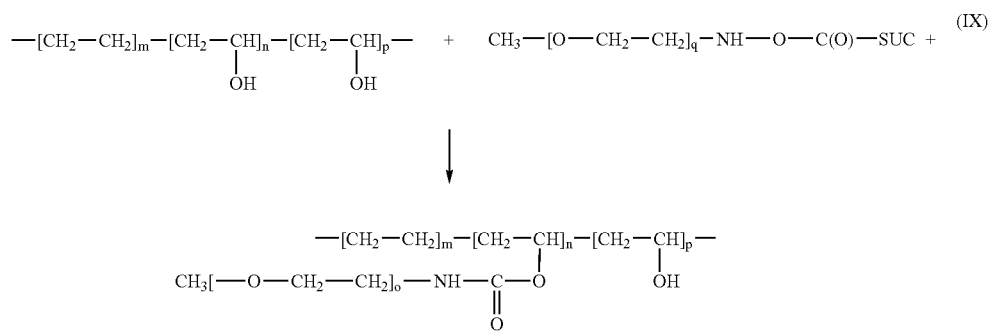

(IX)

The conditions under which reactions (VIII) and (IX) are conducted can be determined by those having ordinary skill in the art. In the EVAL/PEG adduct that is the product of reaction (IX), EVAL and mPEG are covalently linked via a hydrolytically urethane linkage. The adduct is expected to have long lasting biocompatibility and non-fouling properties.

Alternatively, a reactive derivative of PEG can be synthesized by activating mPEG-NH$_2$ with aliphatic diisocyanates instead of N,N'-disuccinimidyl carbonate. For example, 1,4-diisocyanatobutane having the formula O=C=N—CH$_2$—CH$_2$—CH$_2$—CH$_2$—N=C=O can be used. The process of activation can be schematically shown as reaction (X):

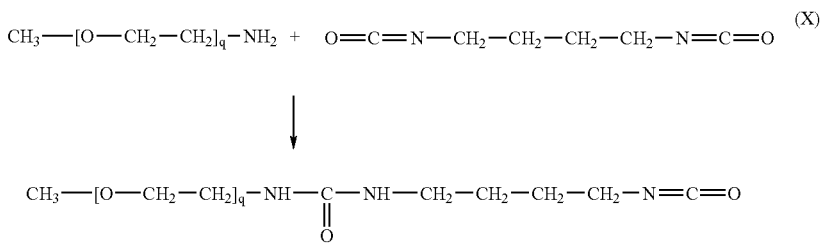

Reaction (X) is carried by slowly adding an equimolar amount of mPEG-NH$_2$ to 1,4-diisocyanatobutane followed by purification of the product of reaction (X) to insure that no unreacted 1,4-diisocyanatobutane remains present. The methods of purification can be determined by those having ordinary skill in the art. After the mPEG-NH$_2$-urethane-isocyanate product of reaction (X) is obtained, it can be reacted with EVAL under conditions that can be determined by those having ordinary skill in the art, yielding a EVAL/PEG adduct in which EVAL and mPEG are covalently linked via a urethane linkage. This adduct can be illustrated by an exemplary formula (XI):

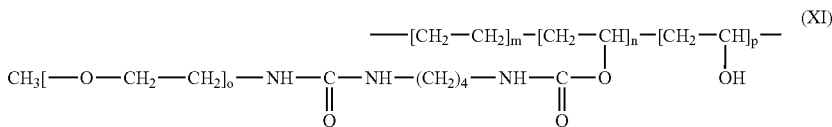

Example 4

Synthesis of EVAL/PEG Adduct with Urea Links

EVAL can be modified by PEG via formation of urea links. The modification is a multi-step process. First, EVAL can be oxidized by a moderately strong oxidant such as chromium oxide or potassium permanganate to form ketone groups. Second, the EVAL containing ketone groups can be reacted with ammonia to form the imine product. The imine product can be reduced by potassium borohydride to form the primary amino-functional EVAL. Finally, isocyanate terminated methoxy-PEG can be then conjugated to the primary amino-functional EVAL to form the urea linkage. The synthesis can be shown below as a reaction scheme (XII):

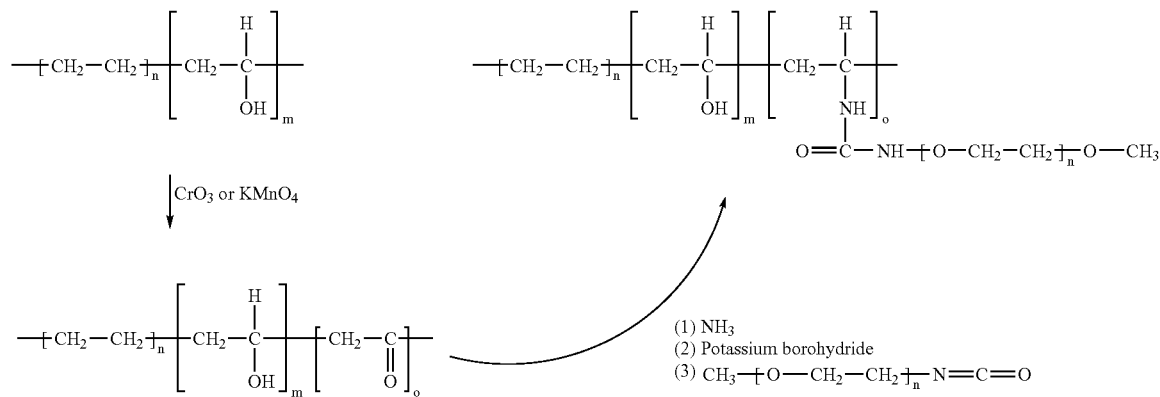

(XII)

As a result of reaction shown by scheme (XII), the final product where EVAL and mPEG are linked, for example, covalently linked in a hydrolytically stable urea structure can be obtained. The final product is an adduct expected to have long lasting biocompatibility and non-fouling properties.

Example 5

Synthesis of EVAL/PEG Adduct with Amide Links

EVAL can be modified by PEG via formation of amide links. In this synthesis, the primary amino-functional EVAL can be made as described in Example 4. Succinimidyl-mPEG can be then linked, for example, covalently linked to the primary amino functional EVAL to form the amide linkage. Succinimidyl derivatives of PEG may be obtained from Nektar Corporation. The synthesis can be shown below as a reaction scheme (XIII):

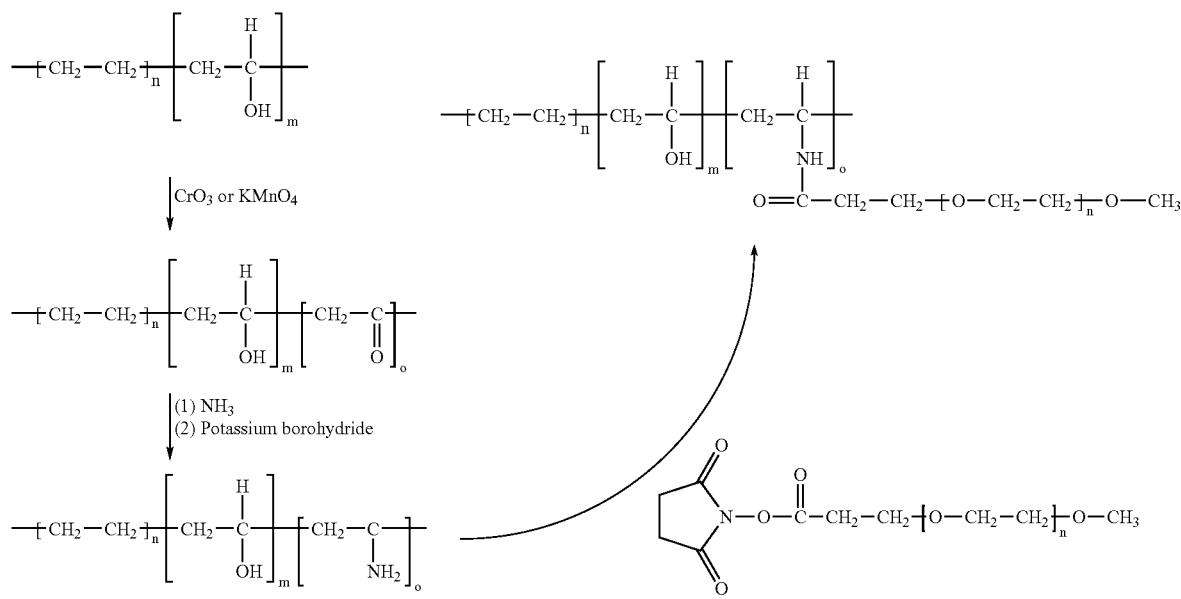

(XIII)

As a result of reaction shown by scheme (XIII), the adduct where EVAL and mPEG are covalently linked in a hydrolytically stable amide structure can be obtained. The final product corresponds to an amide shown in Table 1, where x=2. The final product is an adduct expected to have long lasting biocompatibility and non-fouling properties.

Example 6

Synthesis of EVAL/Hyaluronate Adduct with Amine Links

Instead of PEG, hyaluronic acid can be used to modify EVAL via formation of amine links. In this synthesis, a dihydrazide derivative of hyaluronic acid, e.g., a dihydrazide derivative of adipic acid-hyaluronate, is prepared first as shown by reaction scheme (XIV).

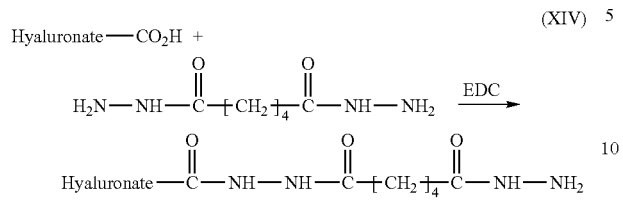

(XIV)

Those having ordinary skill in the art can determine conditions for carrying out the reaction (XIV).

In reaction (XIV), the abbreviation "hyaluronate" stands for hyaluronic acid less a carboxyl group; "hyaluronate-$CO_2H$" is hyaluronic acid. EDC is an abbreviation referring to 1-ethyl-3(3-dimethylaminopropyl) carbodiimide, also known as carbodiimide. EDC is manufactured by Pierce Corp., of Rockford, Ill.

A ketone derivative of EVAL can be prepared by oxidizing EVAL using chromium oxide or potassium permanganate as shown in Example 4 and 5. The product of reaction (XIV) containing a free hydrazide group can then be reacted with the ketone groups via reductive amination in the presence of a strong reducing agent, such as potassium borohydride, $NaBH_4$. The process of reductive amination can be illustrated by the reaction scheme (XV):

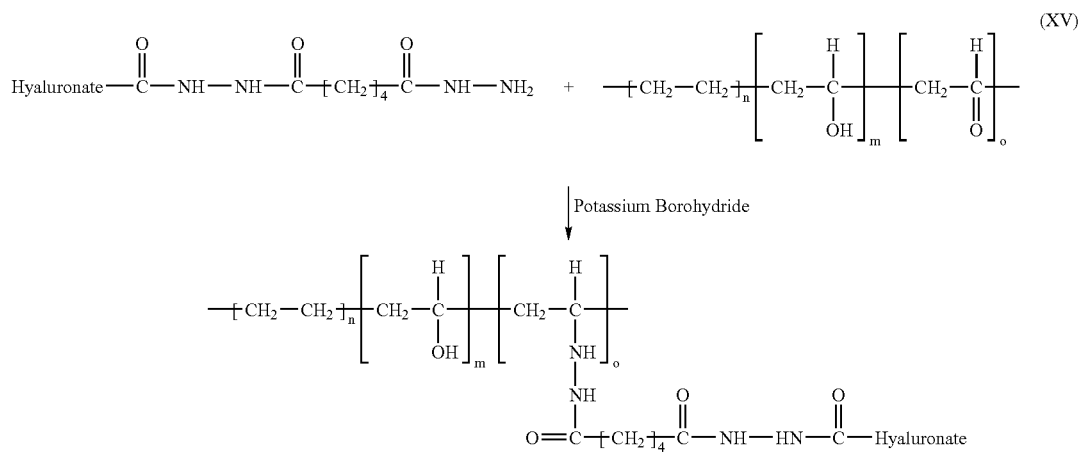

(XV)

As a result of reaction shown by scheme (XV), the final product where EVAL and hyaluronate are covalently linked in a hydrolytically stable amine structure can be obtained. The final product is an adduct expected to have long lasting biocompatibility and non-fouling properties.

Example 7

Synthesis of EVAL/Heparin Adduct with Amine Links

Instead of using PEG, heparin can be used to modify EVAL via formation of amine links. To modify EVAL, aldehyde-terminated heparin can be prepared by oxidative cleavage of heparin using sodium periodate or nitrous acid. Those having ordinary skill in the art can determine conditions for carrying the reaction of oxidation of heparin.

The primary amino-functional EVAL can then be made as described in Example 4. Aldehyde-terminated heparin can be then conjugated to the primary amino functional EVAL via reductive amination using potassiumborohydride, sodium borohydride, or sodium cyanoborohydride, to form the amine linkage, as shown below by a reaction scheme (XVI):

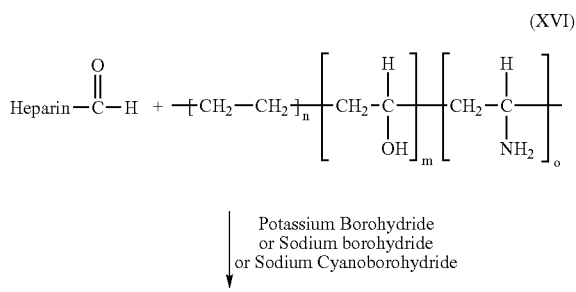

(XVI)

-continued

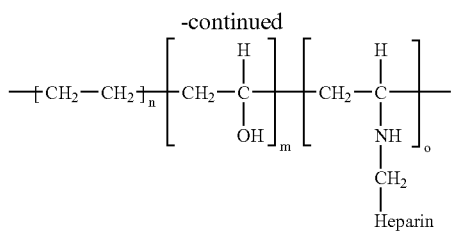

As a result of reaction shown by scheme (XVI), the final product where EVAL and heparin are covalently linked in a hydrolytically stable amine structure can be obtained. The final product is an adduct expected to have long lasting biocompatibility and non-fouling properties.

Example 8

Fabrication of the Coating

The polymer of Example 1 can be dissolved in a mixture of solvents comprising 50% DMSO and 50% DMAC (by weight) to form a 2% solution. All percentage amounts are by weight. A spray apparatus, such as an EFD 780S spray nozzle with a VALVEMATE 7040 control system, manufactured by EFD, Inc. of East Providence, R.I. can be used to apply the polymer solution to a stent. The EFD 780S spray nozzle is an air-assisted external mixing atomizer. The composition can be atomized by air and applied to the stent surfaces. During the process of applying the composition, the stent can be optionally rotated about its longitudinal axis, at a speed of about 50 to about 150 rpm. The stent can also be linearly moved along the same axis during the application.

The 2% solution of the polymer can be applied to a 13-mm TETRA stent (available from Guidant Corporation) in a series of 10-second passes, to deposit 10 μg of coating per spray pass. Between the spray passes, the stent can be dried for 10 seconds using flowing air with a temperature of 80° C. Five spray passes can be applied to form a 50 μg primer layer, followed by baking the primer layer at 140° C. for one hour.

A drug containing formulation can be prepared comprising 2% of the polymer, 1.33% of a derivative of rapamycin and 96.67% of a mixture of solvents comprising 50% DMSO and 50% DMAC. In a manner similar to the application of the primer layer, seventy spray passes can be performed to form a 700 μg drug-polymer layer, followed by baking the drug-polymer layer at 50° C. for 2 hours.

Finally, a topcoat composition to control the drug release rate can be prepared, comprising 2% of the polymer and 98% of a mixture of solvents comprising 80% DMAC and 20% pentane. In a manner similar to the application of the primer layer and the drug-polymer layer, fifteen spray passes can be performed to form a 150 μg topcoat layer, followed by final baking at 50° C. for 2 hours.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A medical article comprising an implantable substrate having a coating deposited on at least a portion of the substrate, the coating comprising a polymer having the formula:

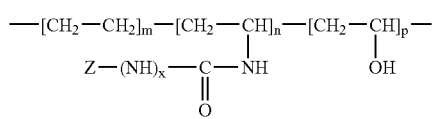

wherein Z is a non-fouling moiety
  m, n, o is each, independently, a positive integer;
  p is a positive integer or p=0;
  the value of m is within a range of between about 30 and about 7,600;
  the value of o is within a range between about 11 and about 680;
  the value of the sum of n and p is within a range of between about 30 and about 7,600;
  the sum of m, n, and p is within a range of between about 700 and about 7,600; and x=0 or x=1.

2. The medical article of claim 1, wherein the non-fouling moiety comprises a compound selected from a group consisting of a poly(alkylene glycol), heparin, poly(vinyl pyrolidone), poly(2-hydroxyethylmethacrylate), poly(2-hydroxypropyl methacrylamide), poly(styrene sulfonate), hyaluronic acid, chondroitan sulfate, and chitosan.

3. The medical article of claim 2, wherein poly(alkylene glycol) is selected from a group consisting of poly(ethylene glycol), poly(1-propylene glycol), poly(2-propylene glycol) and poly(tetramethylene glycol).

4. The medical article of claim 1, wherein the implantable substrate is a stent.

5. The medical article of claim 1, wherein a ratio between n and p is between about 1:19 and about 1:3.

* * * * *